(12) United States Patent
He et al.

(10) Patent No.: US 12,345,665 B1
(45) Date of Patent: Jul. 1, 2025

(54) CALCULATION METHOD FOR FRACTAL DIMENSION OF SHALE PORES

(71) Applicants: Southwest Petroleum University, Chengdu (CN); China University of Geosciences, Wuhan, Wuhan (CN); Jiangxi Provincial Shale Gas Investment Company, Ltd, Nanchang (CN)

(72) Inventors: Xinyang He, Chengdu (CN); Kun Zhang, Chengdu (CN); Shu Jiang, Wuhan (CN); Hulin Niu, Chengdu (CN); Weiwei Liu, Nanchang (CN); Songyang Wan, Nanchang (CN); Chengzao Jia, Chengdu (CN); Yan Song, Chengdu (CN); Xiong Ding, Chengdu (CN); Xueying Wang, Chengdu (CN); Yi Shu, Wuhan (CN); Tianyou Zhi, Nanchang (CN); Daiyu Wu, Nanchang (CN); Sihong Cheng, Nanchang (CN); Yongjun Li, Nanchang (CN); Yiting Qiao, Chengdu (CN); Yi Zhang, Chengdu (CN); Jiayi Liu, Chengdu (CN); Lei Chen, Chengdu (CN); Xuefei Yang, Chengdu (CN); Fengli Han, Chengdu (CN); Weishi Tang, Chengdu (CN); Jingru Ruan, Chengdu (CN); Hengfeng Gou, Chengdu (CN); Yi Xiao, Chengdu (CN); Lintao Li, Chengdu (CN); Yipeng Liu, Chengdu (CN); Ping Liu, Chengdu (CN); Zeyun Wang, Chengdu (CN); Laiting Ye, Chengdu (CN); Meijia Wu, Chengdu (CN); Lu Lu, Chengdu (CN)

(73) Assignees: SOUTHWEST PETROLEUM UNIVERSITY, Chengdu (CN); CHINA UNIVERSITY OF GEOSCIENCES, WUHAN, Wuhan (CN); JIANGXI PROVINCIAL SHALE GAS. INVESTMENT COMPANY, LTD, Nanchang (CN)

( * ) Notice: Subject to any disclaimer, the term of this patent is extended or adjusted under 35 U.S.C. 154(b) by 0 days.

(21) Appl. No.: 18/989,727

(22) Filed: Dec. 20, 2024

(30) Foreign Application Priority Data

Mar. 13, 2024 (CN) .......................... 202410282718.8

(51) Int. Cl.
*G01N 23/20* (2018.01)
*G01N 33/24* (2006.01)

(52) U.S. Cl.
CPC ............. *G01N 23/20* (2013.01); *G01N 33/24* (2013.01); *G01N 2223/616* (2013.01)

(58) Field of Classification Search
CPC ... G01N 23/20; G01N 33/24; G01N 2223/616
See application file for complete search history.

(56) References Cited

U.S. PATENT DOCUMENTS

| | | | |
|---|---|---|---|
| 11,987,855 B2* | 5/2024 | Bao | G06N 5/00 |
| 2020/0173902 A1* | 6/2020 | Wang | G01N 15/08 |
| 2020/0292387 A1* | 9/2020 | Shiokawa | G01J 3/0224 |

OTHER PUBLICATIONS

Li, CN-117518243, English Translation (Year: 2024).*
Cao, Characterization of pore structure and fractal dimension of Paleozoic shales from the northeastern Sichuan Basin, China, Journal of Natural Gas Science and Engineering 35 (2016) 882-895 (Year: 2016).*

* cited by examiner

*Primary Examiner* — Michael J Dalbo
(74) *Attorney, Agent, or Firm* — WPAT, PC

(57) ABSTRACT

A calculation method for fractal dimensions of shale pores includes steps as follows. S1: multiple shale samples from a target stratum of a study area are obtained, parameter values of geological parameters of each of the multiple shale samples are obtained, followed by dividing the multiple shale samples into target shale samples and experimental shale samples. S2: PCA is performed on the parameter values to obtain principal components representing a variation of the geological parameters. fractal dimensions are calculated based on an existing fractal dimension calculation method. S3: the principal components are used as independent variables and the fractal dimensions are used as dependent variables, followed by performing regression analysis to obtain a quantitative calculation model. S4: the fractal dimensions of the target shale sample are calculated according to the parameter values and the quantitative calculation model for the fractal dimension based on the parameter values.

6 Claims, No Drawings

CALCULATION METHOD FOR FRACTAL DIMENSION OF SHALE PORES

CROSS-REFERENCE TO RELATED APPLICATION

This application claims priority to Chinese patent application No. CN 202410282718.8, filed to China National Intellectual Property Administration (CNIPA) on Mar. 13, 2024, which is herein incorporated by reference in its entirety.

TECHNICAL FIELD

The disclosure relates to the technical field of oil and gas exploration and development, and particularly to a calculation method for fractal dimensions of shale pores.

BACKGROUND

Shale oil and gas resources, as an important component of China's energy strategy, have a decisive impact on the adsorption, seepage, and migration processes of oil and gas due to the abundant micro-nanoscale pores in their reservoirs. The fractal dimension of pores is a key quantitative indicator for studying shale reservoirs. It can reveal the heterogeneity and complexity of the pore structure, effectively evaluate the permeability of the reservoir, comprehensively reflect the characteristics of the pore structure, evaluate the development effect of the reservoir, and provide a scientific basis for the exploration and development of shale oil and gas.

At present, there are mainly three methods for calculating the fractal dimension of pores: mercury intrusion porosimetry, nuclear magnetic resonance (NMR), and small-angle neutron scattering (SAXS). The mercury intrusion porosimetry is only applicable to large pores with a diameter greater than 50 nanometers (nm) and is not suitable for mesopores and micropores with a diameter less than 50 nm, which may lead to a bias in the comprehensive understanding of the pore structure. The NMR requires expensive equipment and professional technical support, resulting in high economic costs. The SAXS has high requirements for the shape and size of the experimental samples and detects structures at the nano to microscale. For smaller or larger structural features, other techniques such as TEM or SEM may be needed to complement the analysis.

SUMMARY

To solve the above issues, the disclosure aims to provide a calculation method for fractal dimensions of shale pores.

The calculation method for fractal dimensions of shale pores include steps as follows:
- S1: obtaining multiple shale samples from a target stratum of a study area, obtaining parameter values of geological parameters of each of the multiple shale samples, and dividing the multiple shale samples into target shale samples and experimental shale samples, wherein the geological parameters comprise a mineral composition, a total organic carbon (TOC) content, a porosity, a permeability, and an average pore size;
- S2: performing principal component analysis (PCA) on the parameter values of the geological parameters of the experimental shale samples to obtain principal components representing a variation of the geological parameters of the experimental shale samples, and calculating fractal dimensions of the experimental shale samples by using an existing fractal dimension calculation method;
- S3: performing regression analysis using the principal components as independent variables and the fractal dimensions of the experimental shale samples as dependent variables to obtain a quantitative calculation model for fractal dimensions based on geological parameters; and
- S4: calculating fractal dimensions of the target shale samples according to the parameter values of the geological parameters of the target shale samples and the quantitative calculation model for fractal dimension based on geological parameters.

In an embodiment, in the S1, the geological parameters include a mineral composition, a total organic carbon (TOC) content, a porosity, a permeability, and an average pore size.

In an embodiment, the obtaining parameter values of geological parameters of each of the multiple shale samples includes: performing an X-ray diffraction whole-rock mineral analysis experiment on the multiple shale samples to obtain a parameter value of the mineral composition of each of the multiple shale samples; performing a TOC content analysis experiment on the multiple shale samples to obtain a parameter value of the TOC content of each of the multiple shale samples; performing a physical property testing experiment on the multiple shale samples to obtain parameter values of the porosity and the permeability of each of the multiple shale samples; and performing one of a nitrogen adsorption experiment, a carbon dioxide adsorption experiment, or a mercury injection experiment to obtain a parameter value of the average pore size of each of the multiple shale samples.

In an embodiment, in the S2, the performing PCA on the parameter values of the geological parameters of the experimental shale samples to obtain principal components representing a variation of the parameter values of the geological parameters of the experimental shale samples includes steps as follows:
- S21: standardizing parameter values of the geological parameters of the experimental shale samples to obtain standardized parameter values of the geological parameters of the experimental shale samples;
- S22: establishing a correlation coefficient matrix between the geological parameters of the experimental shale samples based on the standardized parameter values of the geological parameters of the experimental shale samples;
- S23: calculating eigenvalues, contribution rates, and cumulative contribution rates of the correlation coefficient matrix;
- S24: determining a number of the principal components representing the variation of the parameters values of the geological parameters of the experimental shale samples and eigenvalues of the principal components based on the cumulative contribution rates;
- S25: calculating eigenvectors of the correlation coefficient matrix based on the eigenvalues of the principal components determined in step S24; and
- S26: obtaining a mathematical expression (11) of the principal components based on the eigenvectors.

In an embodiment, in the S21, formulas (1)-(3) as follows are used to perform the standardizing parameter values of the geological parameters of the experimental shale:

$$Zx_{ij} = \frac{x_{ij} - \bar{x}_j}{S_j} (i = 1, 2, \ldots, n; j = 1, 2, \ldots, m) \tag{1}$$

$$\bar{x}_j = \frac{1}{n}\sum_{i=1}^{n} x_{ij} \tag{2}$$

$$S_j = \frac{1}{n-1}\sum_{i=1}^{n}(x_{ij} - \bar{x}_j) \tag{3}$$

where $Zx_{ij}$ represents a standardized parameter value of a j-th geological parameter of an i-th sample of the experimental shale samples; $x_{ij}$ represents a parameter value of the j-th geological parameter of the i-th sample of the experimental shale samples; $\bar{x}_j$ represents a sample mean of the j-th geological parameter of the experimental shale samples; $S_j$ represents a sample standard deviation of the j-th geological parameter of the experimental shale samples; n represents a number of the experimental shale samples; and m represents a number of the geological parameters of the experimental shale samples.

In an embodiment, in the S22, the correlation coefficient matrix is expressed by formulas (4)-(8) as follows:

$$R = (r_{AB})_{m \times m} \tag{4}$$

$$r_{AB} = \frac{Cov(A, B)}{\sigma_A \times \sigma_B} \tag{5}$$

$$Cov(A, B) = \frac{\sum_{i=1}^{n}(A_i - \bar{A})(B_i - \bar{B})}{n-1} \tag{6}$$

$$\sigma_A = \sqrt{\frac{\sum_{i=1}^{n}(A_i - \bar{A})^2}{n-1}} \tag{7}$$

$$\sigma_B = \sqrt{\frac{\sum_{i=1}^{n}(B_i - \bar{B})^2}{n-1}} \tag{8}$$

where R represents the correlation coefficient matrix; $r_{AB}$ represents a correlation coefficient between a geological parameter A and a geological parameter B; Cov(A, B) represents a covariance between the geological parameter A and the geological parameter B; $\sigma_A$ represents a standard deviation of the geological parameter A, $\sigma_B$ represents a standard deviation of the geological parameter B, $A_i$ and $B_i$ represent values of the i-th sample of the geological parameter A and the geological parameter B, respectively; $\bar{A}$ represents a sample mean of the geological parameter A of the experimental shale samples; and $\bar{B}$ represents a sample mean of the geological parameter B of the experimental shale samples.

In an embodiment, in the S23, when the eigenvalues of the correlation coefficient matrix are calculated, a characteristic equation (9) of the correlation coefficient matrix is as follows:

$$|R - \lambda E| = 0 \tag{9}$$

where $\lambda$ represents one of the eigenvalues of the correlation coefficient matrix, and E represents an identity matrix; and each of the contribution rates is calculated using a formula (10) as follows:

$$D = \frac{\lambda_k}{\sum_{k=1}^{m} \lambda_k} \tag{10}$$

where D represents the contribution rate, and $\lambda_k$ represents a k-th eigenvalue of the eigenvalues of the correlation coefficient matrix.

In an embodiment, in the S26, the mathematical expression (11) is expressed as follows:

$$F_{ik} = \sum_{j=0}^{m} Zx_{ij} \frac{u_{kj}}{\sqrt{\lambda_k}} \tag{11}$$

where $F_{ik}$ represents a k-th principal component of the i-th sample of the experimental shale samples; and $u_{kj}$ represents a j-th element in a k-th eigenvector of the eigenvectors.

In an embodiment, in the S2, the existing fractal dimension calculation method is one of a Frenkel-Halsey-Hill (FHH) equation, a microporous medium fractal theory, or a Menger sponge model.

In an embodiment, the performing the regression analysis includes performing the regression analysis by using a multiple linear regression analysis method.

The beneficial effects of the disclosure are as follows.

The disclosure can be applied to the calculation of fractal dimensions in the full aperture range, and the calculation results are accurate without special requirements for experimental samples, which can reduce economic costs.

DETAILED DESCRIPTION OF EMBODIMENTS

The disclosure will be further explained in conjunction with the embodiments. It should be noted that, in the absence of conflicts, the embodiments and technical features in the disclosure can be combined with each other. It should be pointed out that, unless otherwise specified, all technical and scientific terms used in the disclosure have the same meanings as those commonly understood by those skilled in the art to which the disclosure belongs. The words "include" or "contain" and similar terms used in the disclosure refer to the elements or objects that appear before the word, including the elements or objects listed after the word and their equivalents, without excluding other elements or objects.

The disclosure provides a calculation method for fractal dimension of shale pores, and the calculation method includes steps S1 to S4 as follows.

S1: multiple shale samples are obtained from a target stratum of a study area, parameter values of geological parameters of each of the multiple shale samples are obtained, and the multiple shale samples are divided into target shale samples and experimental shale samples.

In an embodiment, the geological parameters include a mineral composition, a TOC content, a porosity, a permeability, and an average pore size.

In an embodiment, the obtaining parameter values of geological parameters of each of the multiple shale samples includes steps as follows. An X-ray diffraction whole-rock mineral analysis experiment is performed on the multiple shale samples to obtain a parameter value of the mineral composition of each of the multiple shale samples, a TOC content analysis experiment is performed on the multiple shale samples to obtain a parameter value of the TOC content of each of the multiple shale samples, a physical property testing experiment is performed on the multiple shale samples to obtain parameter values of the porosity and the permeability of each of the multiple shale samples, and one of a nitrogen adsorption experiment, a carbon dioxide adsorption experiment, or a mercury injection experiment is performed to obtain a parameter value of the average pore size of each of the multiple shale samples. It should be noted that the method adopted in the embodiment is only the preferred method of the disclosure, and other methods in the related art that can obtain the geological parameters can also be applied to the disclosure. In addition, the geological parameters of the embodiment are only the preferred geological parameters of the disclosure. In addition to the geological parameters of the embodiment, other geological parameters that may affect the fractal dimensions can also be applied to the disclosure.

S2: PCA is performed on the parameter values of the geological parameters of the experimental shale samples to obtain principal components representing a variation of the geological parameters of the experimental shale samples. The fractal dimensions of the experimental shale samples are calculated by using an existing fractal dimension calculation method.

In an embodiment, the performing PCA on the parameter values of the geological parameters of the experimental shale samples to obtain principal components representing a variation of the parameter values of the geological parameters of the experimental shale samples includes steps S21 to S26 as follow.

S21: parameter values of the geological parameters of the experimental shale samples are standardized to obtain parameter values of the geological parameters of the experimental shale samples.

In an embodiment, formulas (1)-(3) as follows are used to standardize the parameter values of the geological parameters of the experimental shale samples.

$$Zx_{ij} = \frac{x_{ij} - \bar{x}_j}{S_j} (i = 1, 2, \ldots, n; j = 1, 2, \ldots, m) \quad (1)$$

$$\bar{x}_j = \frac{1}{n}\sum_{i=1}^{n} x_{ij} \quad (2)$$

$$S_j = \frac{1}{n-1}\sum_{i=1}^{n}(x_{ij} - \bar{x}_j) \quad (3)$$

where $Zx_{ij}$ represents a standardized parameter value of a j-th geological parameter of an i-th sample of the experimental shale samples; $x_{ij}$ represents a parameter value of the j-th geological parameter of the i-th sample of the experimental shale samples; $\bar{x}_j$ represents a sample mean of the j-th geological parameter of the experimental shale samples; $S_j$ represents a sample standard deviation of the j-th geological parameter of the experimental shale samples; n represents a number of the experimental shale samples; and m represents a number of the geological parameters of the experimental shale samples.

S22: a correlation coefficient matrix between the geological parameters of the experimental shale samples is established based on the standardized parameter values of the geological parameters of the experimental shale samples.

In an embodiment, the correlation coefficient matrix is expressed by formulas (4)-(8) as follows:

$$R = (r_{AB})_{m \times m} \quad (4)$$

$$r_{AB} = \frac{Cov(A, B)}{\sigma_A \times \sigma_B} \quad (5)$$

$$Cov(A, B) = \frac{\sum_{i=1}^{n}(A_i - \bar{A})(B_i - \bar{B})}{n - 1} \quad (6)$$

$$\sigma_A = \sqrt{\frac{\sum_{i=1}^{n}(A_i - \bar{A})^2}{n - 1}} \quad (7)$$

$$\sigma_B = \sqrt{\frac{\sum_{i=1}^{n}(B_i - \bar{B})^2}{n - 1}} \quad (8)$$

where R represents the correlation coefficient matrix; $r_{AB}$ represents a correlation coefficient between a geological parameter A and a geological parameter B; Cov(A, B) represents a covariance between the geological parameter A and the geological parameter B; $\sigma_A$ represents a standard deviation of the geological parameter A, $\sigma_B$ represents a standard deviation of the geological parameter B, $A_i$ and $B_i$ represent values of the i-th sample of the geological parameter A and the geological parameter B, respectively; $\bar{A}$ represents a sample mean of the geological parameter A of the experimental shale samples; and $\bar{B}$ represents a sample mean of the geological parameter B of the experimental shale samples.

S23: eigenvalues, contribution rates, and cumulative contribution rates of the correlation coefficient matrix are calculated.

In an embodiment, when the eigenvalues of the correlation coefficient matrix are calculated, a characteristic equation (9) of the correlation coefficient matrix is as follows:

$$|R - \lambda E| = 0 \quad (9)$$

where $\lambda$ one of the eigenvalues of the correlation coefficient matrix, and E represents an identity matrix; and where each of the contribution rates is calculated using a formula (10) as follows:

$$D = \frac{\lambda_k}{\sum_{k=1}^{m} \lambda_k} \quad (10)$$

where D represents the contribution rate, $\lambda_k$ represents a k-th eigenvalue of the eigenvalues of the correlation coefficient matrix.

It should be noted that in the above embodiment, m in formula (10) is the total number of the eigenvalues, which is numerically the same as the number of the geological parameters. Therefore, it has not been repeatedly explained.

S24: a number of the principal components representing the variation of the parameters values of the geological parameters of the experimental shale samples and eigenvalues of the principal components are determined based on the cumulative contribution rates.

S25: eigenvectors of the correlation coefficient matrix are calculated based on the eigenvalues of the principal components determined in step S24.

S26: a mathematical expression (11) of the principal components is obtained based on the eigenvectors.

In an embodiment, the mathematical expression (11) is expressed as follows:

$$F_{ik} = \sum_{j=0}^{m} Zx_{ij} \frac{u_{kj}}{\sqrt{\lambda_k}} \quad (11)$$

where $F_{ik}$ represents a k-th principal component of the i-th sample of the experimental shale samples; and $u_{kj}$ represents a j-th element in a k-th eigenvector of the eigenvectors.

It should be noted that in the above embodiment, m in the mathematical expression (11) is the number of elements in the feature vector, which is numerically the same as the number of the geological parameters. Therefore, it has not been repeatedly explained.

In an embodiment, the existing fractal dimension calculation method is one of a FHH equation, a microporous medium fractal theory, or a Menger sponge model. It should be noted that the FHH equation, the microporous media fractal theory, and the Menger sponge model calculation are all existing techniques for calculating the fractal dimensions, and the specific methods will not be repeated here. In addition, besides the preferred calculation method in the embodiment, other existing techniques for obtaining the fractal dimensions can also be applied to the disclosure.

S3: the principal components are used as independent variables and the fractal dimensions of the experimental shale samples are used as dependent variables, followed by performing regression analysis to obtain a quantitative calculation model for the fractal dimensions based on the geological parameters.

In an embodiment, a multiple linear regression analysis method is used for the regression analysis. It should be noted that if the number of principal components determined in the step S24 is one, then a simple linear regression analysis method can be used for the regression analysis. Additionally, other nonlinear regression analysis methods may also be applicable to the disclosure, mainly depending on the specific values of the independent and dependent variables.

S4: fractal dimensions of the target shale sample are calculated according to the parameter values of the geological parameters of the target shale sample and the quantitative calculation model for the fractal dimension based on the geological parameters.

The obtained fractal dimensions are used to quantitatively describe a strength of heterogeneity in pore structure. A smaller the fractal dimension of, the better the sorting of pores, the weaker the heterogeneity, and the better the connectivity of pores, which is more conducive to oil and gas permeability. Therefore, the target stratum of the study area with the weaker heterogeneity is selected based on the obtained fractal dimensions as an optimal stratum for oil and gas exploration and development, and then oil and/or gas are exploited from the optimal stratum.

In an embodiment, a mud shale of the Da'an Zhai Formation in the Lower Jurassic Zi Liu Jing Group in the northeastern Sichuan Basin is taken as an example, fractal dimensions of shale pores are calculated using the calculation method of disclosure, which specifically includes steps as follows.

(1) Multiple experimental shale samples from a target stratum of a study area are obtained, and its parameter values of geological parameters and fractal dimensions are further obtained.

In the embodiment, the X-ray diffraction whole-rock mineral analysis experiment is performed on the multiple experimental shale samples to obtain the mineral composition of the shale (including quartz, feldspar, carbonate minerals, and clay minerals). The TOC content analysis experiment is performed on the multiple shale samples to obtain a parameter value of the TOC content of each of the multiple shale samples. The physical property testing experiment is performed on the multiple shale samples to obtain parameter values of the porosity and the permeability of each of the multiple shale samples. The nitrogen adsorption experiment is performed to obtain a parameter value of the average pore size of each of the multiple shale samples. The fractal dimensions of the shale are calculated according to the FHH equation, and the results are shown in Table 1.

TABLE 1

Parameter values of original geological parameters and fractal dimensions of experimental shale samples

| Sample number | TOC (%) | Quartz (%) | Feldspar (%) | Carbonate mineral (%) | Clay mineral (%) | Porosity (%) | Permeability (×10−3 μm) | Average pore size (nm) | Fractal dimension |
|---|---|---|---|---|---|---|---|---|---|
| 1 | 1.72 | 35.7 | 11.8 | 9.6 | 42.9 | 3.67 | 0.46 | 9.94 | 2.5304 |
| 2 | 1.59 | 36.0 | 8.0 | 30.1 | 25.9 | 3.58 | 0.41 | 9.51 | 2.5524 |
| 3 | 1.93 | 33.4 | 12.6 | 6.9 | 47.1 | 3.86 | 0.52 | 10.9 | 2.4655 |
| 4 | 1.81 | 45.3 | 3.7 | 18.7 | 32.3 | 3.78 | 0.49 | 10.48 | 2.5086 |
| 5 | 1.50 | 36.4 | 6.2 | 10.1 | 47.3 | 3.47 | 0.38 | 9.20 | 2.5948 |
| 6 | 2.24 | 31.5 | 6.1 | 23.9 | 38.5 | 4.21 | 0.60 | 11.87 | 2.3433 |
| 7 | 2.14 | 30.3 | 11.3 | 3.9 | 54.5 | 4.12 | 0.57 | 11.57 | 2.3933 |
| 8 | 2.32 | 27.5 | 13.7 | 14.5 | 44.3 | 4.32 | 0.64 | 12.02 | 2.3195 |
| 9 | 2.02 | 39.5 | 8.7 | 4.2 | 47.6 | 3.99 | 0.55 | 11.25 | 2.4232 |
| 10 | 1.22 | 41 | 3.7 | 21.9 | 33.4 | 3.23 | 0.34 | 8.31 | 2.6922 |
| 11 | 1.00 | 44.1 | 7.1 | 26.5 | 22.3 | 3.04 | 0.29 | 7.23 | 2.7365 |
| 12 | 0.83 | 37.1 | 7.6 | 32.3 | 23.0 | 2.78 | 0.25 | 6.39 | 2.7964 |
| 13 | 0.92 | 42.2 | 1.8 | 14.7 | 41.3 | 2.89 | 0.27 | 6.82 | 2.7690 |
| 14 | 1.32 | 41.0 | 6.9 | 18.0 | 34.1 | 3.32 | 0.36 | 8.76 | 2.6461 |
| 15 | 1.09 | 48.5 | 6.8 | 11.1 | 33.6 | 3.15 | 0.30 | 7.75 | 2.7240 |

(2) The parameter values of the geological parameters of the experimental shale samples are standardized using formulas (1)-(3).

In the embodiment, the parameter values of the geological parameters of the experimental shale samples are standardized using formulas (1)-(3), and the results are shown in Table 2.

TABLE 2

Standardized parameter values of geological parameters of experimental shale samples

| Sample number | TOC | Quartz | Feldspar | Carbonate mineral | Clay mineral | Porosity | Permeability | Average pore size |
|---|---|---|---|---|---|---|---|---|
| 1 | 0.2882 | −0.3854 | 1.1871 | −0.7523 | 0.5189 | 0.2245 | 0.2445 | 0.2516 |
| 2 | 0.0268 | −0.334 | 0.0778 | 1.5069 | −1.2359 | 0.0397 | −0.1456 | 0.0230 |
| 3 | 0.7104 | −0.7765 | 1.4207 | −1.0499 | 0.9522 | 0.6147 | 0.7126 | 0.7620 |
| 4 | 0.4691 | 1.2469 | −1.1774 | 0.2505 | −0.5752 | 0.4504 | 0.4785 | 0.5387 |
| 5 | −0.1541 | −0.2664 | −0.4476 | −0.6972 | 0.9729 | −0.1862 | −0.3797 | −0.1418 |
| 6 | 1.3336 | −1.0996 | −0.4768 | 0.8236 | 0.0647 | 1.3334 | 1.3368 | 1.2777 |
| 7 | 1.1326 | −1.3036 | 1.0412 | −1.3805 | 1.7159 | 1.1486 | 1.1027 | 1.1182 |
| 8 | 1.4945 | −1.7797 | 1.7418 | −0.2123 | 0.6633 | 1.5593 | 1.6489 | 1.3574 |
| 9 | 0.8913 | 0.2607 | 0.2822 | −1.3475 | 1.0038 | 0.8817 | 0.9466 | 0.9481 |
| 10 | −0.7171 | 0.5158 | −1.1774 | 0.6032 | −0.4617 | −0.6790 | −0.691 | −0.6149 |
| 11 | −1.1594 | 1.0429 | −0.1849 | 1.1101 | −1.6072 | −1.0692 | −1.08193 | −1.1891 |
| 12 | −1.5012 | −0.1474 | −0.0389 | 1.7493 | −1.5350 | −1.6031 | −1.3940 | −1.6356 |
| 13 | −1.3202 | 0.7198 | −1.7320 | −0.1903 | 0.3536 | −1.3772 | −1.2380 | −1.4070 |
| 14 | −0.5160 | 0.5158 | −0.2433 | 0.1734 | −0.3894 | −0.4942 | −0.5358 | −0.3757 |
| 15 | −0.9784 | 1.7910 | −0.2725 | −0.5870 | −0.4410 | −0.8433 | −1.0039 | −0.9126 |

(3) Based on the standardized parameter values of the geological parameters in the Table 2, a correlation coefficient matrix between the geological parameters of the experimental shale samples based on the standardized parameter values of the geological parameters of the experimental shale samples is established using formulas (4)-(8). In the embodiment, the established correlation coefficient matrix (12) is as follows.

$$R = \begin{bmatrix} 1 & -0.696 & 0.576 & -0.449 & 0.639 & 0.998 & 0.995 & 0.997 \\ -0.696 & 1 & -0.675 & 0.152 & -0.511 & -0.676 & -0.696 & -0.655 \\ 0.576 & -0.675 & 1 & -0.383 & 0.415 & 0.573 & 0.583 & 0.556 \\ -0.449 & 0.152 & -0.383 & 1 & -0.893 & -0.446 & -0.438 & -0.471 \\ 0.639 & -0.511 & 0.415 & -0.893 & 1 & 0.626 & 0.627 & 0.642 \\ 0.998 & -0.676 & 0.573 & -0.446 & 0.626 & 1 & 0.993 & 0.996 \\ 0.995 & -0.696 & 0.583 & -0.438 & 0.627 & 0.993 & 1 & 0.989 \\ 0.997 & -0.655 & 0.556 & -0.471 & 0.642 & 0.996 & 0.989 & 1 \end{bmatrix} \quad (12)$$

(4) Eigenvalues of the correlation coefficient matrix are calculated according to the formula (9), contribution rates of the correlation coefficient matrix are calculated according to the formula (10), and cumulative contribution rates are obtained. In the embodiment, the calculation results of the eigenvalues, contribution rates, and cumulative contribution rates are shown in Table 3 as follows.

(5) A number of principal components and their corresponding eigenvalues are determined based on the calculation results of the cumulative contribution rates in Table 3.

In statistics, it is stipulated that when the cumulative contribution rate is ≥90%, the principal components have a good explanatory effect on the original geological parameters. Therefore, in the embodiment, the number of principal components should be the number corresponding to a cumulative contribution rate of ≥90%. In the Table 3, the principal components are sorted from largest to smallest according to the contribution rates. From the Table 3, it can be seen that when extracting 3 principal components, the cumulative contribution rate reaches 95.33%, which means that extracting 3 principal components can explain 95.33% of the geological information of the 8 original geological variables. The explanatory effect on the original geological parameters is good, achieving the purpose of dimensionality reduction while retaining most of the information from the original geological parameters. Therefore, in the embodiment, 3 principal components are extracted, denoted as $F_1$, $F_2$, and $F_3$, representing the 8 original geological parameters.

(6) The number of the principal components and their corresponding eigenvalues are determined based on the cumulative contribution rates.

In the embodiment, according to the calculation results of the cumulative contribution rates of the step (5), it can be

TABLE 3

Calculation results of eigenvalues, contribution rates, and cumulative contribution rates

| Principal component | Eigenvalue | Contribution rates (%) | Cumulative contribution rate (%) |
|---|---|---|---|
| $F_1$ | 5.718 | 71.470 | 71.470 |
| $F_2$ | 1.188 | 14.847 | 86.317 |
| $F_3$ | 0.721 | 9.013 | 95.330 |
| $F_4$ | 0.360 | 4.498 | 99.828 |
| $F_5$ | 0.010 | 0.124 | 99.952 |
| $F_6$ | 0.003 | 0.038 | 99.990 |
| $F_7$ | 0.001 | 0.010 | 100.000 |
| $F_8$ | $1.08420217 \times 10^{-18}$ | $1.355 \times 10^{-17}$ | 100.000 | known that the eigenvalues corresponding to $F_1$, $F_2$, and $F_3$ are $\lambda_1=5.718$, $\lambda_2=1.188$, $\lambda_3=0.721$.

(7) Based on the eigenvalues determined in step (6), the eigenvectors of the correlation coefficient matrix are calculated.

In the embodiment, the eigenvalues $\lambda_k$ corresponding to the principal component $F_i$ selected in step (6) are substituted into the characteristic formula (9) to obtain the eigenvector $u_i=(i_{i1}, u_{i2}, u_{i3}, u_{i4}, u_{i5}, u_{i6}, u_{i7}, u_{i8})$ of the eigenvalue $\lambda_k$.

In the embodiment, 3 principal components are extracted, and the eigenvectors $u_1$, $u_2$, $u_3$ corresponding to $\lambda_1$, $\lambda_2$, $\lambda_3$ for the 8 original geological parameters are solved as follows:

$$u_1=(0.9674,-0.7580,0.6920,-0.5956,0.7732,0.9616, 0.9633,0.9607) \quad (13)$$

$$u_2=(0.1461,-0.3595,0.1389,0.7929,-0.5734,0.1480, 0.1590,0.1146) \quad (14)$$

$$u_3=(0.2016,0.3698,-0.6272,0.0747,-0.0727,0.2159, 0.1938,0.2350) \quad (15)$$

(8) Based on the eigenvectors determined in step (7), combine with mathematical expression (11) to obtain a mathematical expression of the principal components. The mathematical expression (16) for the 3 principal components $F_1$, $F_2$, and $F_3$ obtained according to mathematical expression (11) is as follows:

$$F_{ik} = \frac{u_{k1}}{\sqrt{\lambda_k}}Zx_{i1} + \frac{u_{k2}}{\sqrt{\lambda_k}}Zx_{i2} + \frac{u_{k3}}{\sqrt{\lambda_k}}Zx_{i3} + \frac{u_{k4}}{\sqrt{\lambda_k}}Zx_{i4} + \frac{u_{k5}}{\sqrt{\lambda_k}}Zx_{i5} + \frac{u_{k6}}{\sqrt{\lambda_k}}Zx_{i6} + \frac{u_{k7}}{\sqrt{\lambda_k}}Zx_{i7} + \frac{u_{k8}}{\sqrt{\lambda_k}}Zx_{i8} \quad (16)$$

In the embodiment, the mathematical expressions for $F_{11}$, $F_{12}$, and $F_{13}$ of sample 1 are as follows:

$$F_{11}=0.4046Zx_{11}+0.4029Zx_{12}+0.4022Zx_{13}+ 0.4018Zx_{14}+\mathbf{0.3234}Zx_{15}-0.3170Zx_{16}+ 0.2894Zx_{17}-0.2491Zx_{18} \quad (17)$$

$$F_{12}=0.1341Zx_{21}+0.1459Zx_{22}+0.1358Zx_{23}+ 0.1052Zx_{24}-0.5262Zx_{25}-0.3299Zx_{26}+ 0.1275Zx_{27}+0.7275Zx_{28} \quad (18)$$

$$F_{13}=0.2374Zx_{31}+0.2282Zx_{32}+0.2542Zx_{33}+ 0.2768Zx_{34}-0.0856Zx_{35}+0.4355Zx_{36}- 0.7386Zx_{37}+0.0880Zx_{38} \quad (19)$$

(9) Based on the mathematical expressions of the principal components in formula (13)-(16), the principal component scores for $F_1$, $F_2$, and $F_3$ for 15 samples are calculated, with the results shown in Table 4.

TABLE 4

| Sample number | principal component score | | |
|---|---|---|---|
| | $F_1$ | $F_2$ | $F_3$ |
| 1 | 0.2426 | −0.0683 | −0.0324 |
| 2 | 0.0530 | 0.7592 | 0.6023 |
| 3 | 0.2575 | 0.0058 | −0.2130 |
| 4 | −0.0024 | 0.7183 | 0.1058 |
| 5 | −0.3320 | −0.7957 | −0.3018 |
| 6 | −0.0890 | 0.6663 | −0.1258 |
| 7 | 0.0357 | −0.3699 | −0.5113 |
| 8 | 0.3719 | 0.4893 | −0.1439 |
| 9 | 0.1263 | 0.0455 | −0.3503 |
| 10 | −0.2989 | −0.1860 | 0.0169 |
| 11 | 0.1183 | 0.2838 | 0.5914 |
| 12 | 0.0262 | −0.0751 | 0.4064 |
| 13 | −0.4827 | −1.2404 | −0.4820 |
| 14 | −0.0630 | 0.0176 | 0.1624 |
| 15 | 0.0365 | −0.2503 | 0.2753 |
| — | — | — | — |

(10) Using the principal component scores from Table 4 as independent variables and the fractal dimensions from Table 1 as dependent variables, a multiple linear regression analysis method is performed to obtain a quantitative calculation model for fractal dimensions based on the geological parameters.

In the embodiment, a multiple linear regression module in SPSS 26.0 software is used to perform the multiple linear regression analysis method, and the obtained quantitative calculation model for fractal dimensions based on the geological parameters is as follows:

$$Y=-0.141 \times F_1-0.240 \times F_2+0.418 \times F_3+2.566 \quad (17)$$

(11) A target shale sample and the parameter values of the geological parameters of the target shale sample for the target stratum in the study area, and fractal dimensions of the target shale sample are calculates using the quantitative calculation model based on the geological parameters as shown in formula (17), and a feasibility test is performed. The results are shown in Table 5.

TABLE 5

Predicting fractal dimensions and relative errors

| | Sample number | | | | | | | | | |
|---|---|---|---|---|---|---|---|---|---|---|
| | 16 | 17 | 18 | 19 | 20 | 21 | 22 | 23 | 24 | 25 |
| TOC (%) | 1.42 | 1.51 | 1.83 | 1.91 | 1.57 | 2.34 | 2.04 | 2.12 | 1.72 | 1.42 |
| Quartz (%) | 30.7 | 36 | 37.4 | 40.7 | 36.1 | 45.5 | 31.7 | 29.7 | 49.5 | 35 |
| Feldspar (%) | 10.8 | 6.5 | 10.5 | 13.7 | 8.2 | 8.1 | 10.3 | 13.7 | 18.7 | 8.7 |
| Carbonate mineral (%) | 13.6 | 30.7 | 16.9 | 8.4 | 12.1 | 13.9 | 7.9 | 10.3 | 4.2 | 21.9 |
| Clay mineral (%) | 44.9 | 26.8 | 35.2 | 37.2 | 43.6 | 32.5 | 50.1 | 46.3 | 27.6 | 34.4 |
| Porosity (%) | 5.67 | 3.58 | 4.26 | 3.78 | 3.41 | 3.74 | 4.12 | 3.52 | 3.67 | 3.71 |
| Permeability ($\times 10^{-3}$ μm) | 0.69 | 0.41 | 0.52 | 0.59 | 0.47 | 0.52 | 0.57 | 0.44 | 0.52 | 0.35 |

TABLE 5-continued

Predicting fractal dimensions and relative errors

| | Sample number | | | | | | | | | |
|---|---|---|---|---|---|---|---|---|---|---|
| | 16 | 17 | 18 | 19 | 20 | 21 | 22 | 23 | 24 | 25 |
| Average pore size(nm) | 9.76 | 10.34 | 10.91 | 9.46 | 11.2 | 10.87 | 11.32 | 11.99 | 10.25 | 11.87 |
| Experimental fractal dimension | 2.6830 | 2.8542 | 2.5959 | 2.3186 | 2.4927 | 2.3696 | 2.3563 | 2.5790 | 2.4678 | 2.8271 |
| Prediction analysis dimension | 2.7994 | 2.8189 | 2.6483 | 2.3208 | 2.4209 | 2.3931 | 2.3831 | 2.5399 | 2.3977 | 2.9378 |
| Relative error | 4.34% | −1.24% | 2.02% | 0.10% | −2.88% | 0.99% | 1.14% | −1.51% | −2.84% | 3.91% |

Note: in Table 5, the term "experimental fractal dimensions" refers to the fractal dimensions calculated using the FHH equation.

From the Table 5, it is evident that the relative errors between the predicted fractal dimensions by the disclosure and the analytical dimensions measured experimentally falls between −2.841% and 4.34%. This demonstrates that the quantitative calculation model for the fractal dimensions based on the geological parameters derived from the disclosure is highly accurate in prediction and robust in practical application.

In the above embodiment, step (1) involves calculating the fractal dimension of shale using the FHH equation, which requires determining relevant parameters from nuclear magnetic resonance (NMR) experiments and then calculating the results of the fractal dimensions using the FHH equation (this is the related art, and the specific steps will not be repeated here). With the quantitative calculation model for the fractal dimensions as shown in formula (17) obtained from the disclosure, it is possible to directly calculate the fractal dimensions of other samples with the same lithology using the model, without the need for further NMR experiments or similar steps. Compared to the related art, the method of the disclosure eliminates experimental procedures and offers a simpler calculation model.

In summary, the disclosure can be applied to the calculation of fractal dimensions across the entire pore size range of the same lithology, thereby improving resolution. By predicting fractal dimensions using the quantitative calculation model based on the geological parameters obtained from the disclosure, it reduces economic costs. The mathematical relationship between the geological parameters and pore fractal dimensions enables accurate prediction of the continuity of pore fractal dimensions in a single well or on a plane. Compared to the related art, the disclosure represents a significant advancement.

The above description is only the preferred embodiment of the disclosure and does not limit the disclosure in any form. Although the disclosure has been disclosed in the preferred embodiment, it is not intended to limit the disclosure. Those skilled in the art who are familiar with this field can use the disclosed technical content to make slight changes or modifications to equivalent embodiments without departing from the scope of the technical solution of the disclosure. Any simple modifications, equivalent changes, and modifications made to the above embodiments based on the technical essence of the disclosure without departing from the technical solution of the disclosure still belong to the scope of the technical solution of the disclosure.

What is claimed is:

1. A calculation method for fractal dimensions of shale pores, the calculation method comprising:
    S1: obtaining multiple shale samples from a target stratum of a study area, obtaining parameter values of geological parameters of each of the multiple shale samples, and dividing the multiple shale samples into target shale samples and experimental shale samples, wherein the geological parameters comprise a mineral composition, a total organic carbon (TOC) content, a porosity, a permeability, and an average pore size;
    S2: performing principal component analysis (PCA) on the parameter values of the geological parameters of the experimental shale samples to obtain principal components representing a variation of the geological parameters of the experimental shale samples, and calculating fractal dimensions of the experimental shale samples by using an existing fractal dimension calculation method;
    wherein the performing PCA on the parameter values of the geological parameters of the experimental shale samples to obtain principal components representing a variation of the parameter values of the geological parameters of the experimental shale samples comprises:
    S21: standardizing parameter values of the geological parameters of the experimental shale samples using formulas (1)-(3) as follows to obtain standardized parameter values of the geological parameters of the experimental shale samples:

$$Zx_{ij} = \frac{x_{ij} - \overline{x}_j}{S_j} (i = 1, 2, \ldots, n; j = 1, 2, \ldots, m) \quad (1)$$

$$\overline{x}_j = \frac{1}{n} \sum_{i=1}^{n} x_{ij} \quad (2)$$

$$S_j = \frac{1}{n-1} \sum_{i=1}^{n} (x_{ij} - \overline{x}_j) \quad (3)$$

where $Zx_{ij}$ represents a standardized parameter value of a j-th geological parameter of an i-th sample of the experimental shale samples; $x_{ij}$ represents a parameter value of the j-th geological parameter of the i-th sample of the experimental shale samples; $\overline{x}_j$ represents a sample mean of the j-th geological parameter of the experimental shale samples; $S_j$ represents a sample standard deviation of the j-th geological parameter of the experimental shale samples; n represents a number of the experimental shale samples; and m represents a number of the geological parameters of the experimental shale samples;

S22: establishing a correlation coefficient matrix between the geological parameters of the experimental shale samples based on the standardized parameter values of the geological parameters of the experimental shale samples, wherein the correlation coefficient matrix is expressed by formulas (4)-(8) as follows:

$$R = (r_{AB})_{m \times m} \tag{4}$$

$$r_{AB} = \frac{Cov(A, B)}{\sigma_A \times \sigma_B} \tag{5}$$

$$Cov(A, B) = \frac{\sum_{i=1}^{n}(A_i - \overline{A})(B_i - \overline{B})}{n - 1} \tag{6}$$

$$\sigma_A = \sqrt{\frac{\sum_{i=1}^{n}(A_i - \overline{A})^2}{n - 1}} \tag{7}$$

$$\sigma_B = \sqrt{\frac{\sum_{i=1}^{n}(B_i - \overline{B})^2}{n - 1}} \tag{8}$$

where R represents the correlation coefficient matrix; $r_{AB}$ represents a correlation coefficient between a geological parameter A and a geological parameter B; Cov(A, B) represents a covariance between the geological parameter A and the geological parameter B; $\sigma_A$ represents a standard deviation of the geological parameter A, $\sigma_B$ represents a standard deviation of the geological parameter B, $A_i$ and $B_i$ represent values of the i-th sample of the geological parameter A and the geological parameter B, respectively; $\overline{A}$ represents a sample mean of the geological parameter A of the experimental shale samples; and $\overline{B}$ represents a sample mean of the geological parameter B of the experimental shale samples;

S23: calculating eigenvalues, contribution rates, and cumulative contribution rates of the correlation coefficient matrix;

where when the eigenvalues of the correlation coefficient matrix are calculated, a characteristic equation (9) of the correlation coefficient matrix is as follows:

$$|R - \lambda E| = 0 \tag{9}$$

where $\lambda$ represents one of the eigenvalues of the correlation coefficient matrix, and E represents an identity matrix; and where each of the contribution rates is calculated using a formula (10) as follows:

$$D = \frac{\lambda_k}{\sum_{k=1}^{m} \lambda_k} \tag{10}$$

where D represents the contribution rate, and $\lambda_k$ represents a k-th eigenvalue of the eigenvalues of the correlation coefficient matrix;

S24: determining a number of the principal components representing the variation of the parameters values of the geological parameters of the experimental shale samples and eigenvalues of the principal components based on the cumulative contribution rates;

S25: calculating eigenvectors of the correlation coefficient matrix based on the eigenvalues of the principal components determined in step S24; and S26: obtaining a mathematical expression (11) of the principal components based on the eigenvectors, wherein the mathematical expression (11) is expressed as follows:

$$F_{ik} = \sum_{j=0}^{m} Zx_{ij} \frac{u_{kj}}{\sqrt{\lambda_k}} \tag{11}$$

where $F_{ik}$ represents a k-th principal component of the i-th sample of the experimental shale samples; and $u_{kj}$ represents a j-th element in a k-th eigenvector of the eigenvectors;

S3: performing regression analysis using the principal components as independent variables and the fractal dimensions of the experimental shale samples as dependent variables to obtain a quantitative calculation model for fractal dimensions based on geological parameters;

S4: calculating fractal dimensions of the target shale samples according to the parameter values of the geological parameters of the target shale samples and the quantitative calculation model for fractal dimension based on geological parameters; and S5: evaluating, based on the fractal dimensions of the target shale samples, a strength of heterogeneity in pore structure of the target stratum of the study area; determining whether the strength of heterogeneity is smaller than a target strength of heterogeneity; and in response to the strength of heterogeneity being smaller than the target strength of heterogeneity, exploring shale oil and gas on the target stratum of the study area.

2. The calculation method for fractal dimension of shale pores as claimed in claim 1, wherein the obtaining parameter values of geological parameters of each of the multiple shale samples comprises:

performing an X-ray diffraction whole-rock mineral analysis experiment on the multiple shale samples to obtain a parameter value of the mineral composition of each of the multiple shale samples;

performing a TOC content analysis experiment on the multiple shale samples to obtain a parameter value of the TOC content of each of the multiple shale samples;

performing a physical property testing experiment on the multiple shale samples to obtain parameter values of the porosity and the permeability of each of the multiple shale samples; and performing one of a nitrogen adsorption experiment, a carbon dioxide adsorption experiment, or a mercury injection experiment to obtain a parameter value of the average pore size of each of the multiple shale samples.

3. The calculation method for fractal dimension of shale pores as claimed in claim 1, wherein, in the S2, the existing fractal dimension calculation method is one of a Frenkel-Halsey-Hill (FHH) equation, a microporous medium fractal theory, or a Menger sponge model.

4. The calculation method for fractal dimension of shale pores as claimed in claim 1, wherein, in the S3, the performing the regression analysis comprises performing the regression analysis by using a multiple linear regression analysis method.

5. A calculation method for fractal dimensions of shale pores, the calculation method comprising:
S1: obtaining multiple shale samples from a target stratum of a study area, obtaining parameter values of geological parameters of each of the multiple shale samples, and dividing the multiple shale samples into target shale samples and experimental shale samples, wherein the geological parameters comprise a mineral composition, a total organic carbon (TOC) content, a porosity, a permeability, and an average pore size, and the obtaining parameter values of geological parameters of each of the multiple shale samples comprises:
performing an X-ray diffraction whole-rock mineral analysis experiment on the multiple shale samples to obtain a parameter value of the mineral composition of each of the multiple shale samples;
performing a TOC content analysis experiment on the multiple shale samples to obtain a parameter value of the TOC content of each of the multiple shale samples;
performing a physical property testing experiment on the multiple shale samples to obtain parameter values of the porosity and the permeability of each of the multiple shale samples; and
performing one of a nitrogen adsorption experiment, a carbon dioxide adsorption experiment, or a mercury injection experiment to obtain a parameter value of the average pore size of each of the multiple shale samples;
S2: performing principal component analysis (PCA) on the parameter values of the geological parameters of the experimental shale samples to obtain principal components representing a variation of the geological parameters of the experimental shale samples, and performing nuclear magnetic resonance (NMR) experiments and calculating fractal dimensions of the experimental shale samples by using an existing fractal dimension calculation method, wherein the existing fractal dimension calculation method is a Frenkel-Halsey-Hill (FHH) equation;
wherein the performing PCA on the parameter values of the geological parameters of the experimental shale samples to obtain principal components representing a variation of the parameter values of the geological parameters of the experimental shale samples comprises:
S21: standardizing parameter values of the geological parameters of the experimental shale samples using formulas (1)-(3) as follows to obtain standardized parameter values of the geological parameters of the experimental shale samples:

$$Zx_{ij} = \frac{x_{ij} - \bar{x}_j}{S_j} (i = 1, 2, \ldots, n; j = 1, 2, \ldots, m) \quad (1)$$

$$\bar{x}_j = \frac{1}{n} \sum_{i=1}^{n} x_{ij} \quad (2)$$

$$S_j = \frac{1}{n-1} \sum_{i=1}^{n} (x_{ij} - \bar{x}_j) \quad (3)$$

where $Zx_{ij}$ represents a standardized parameter value of a j-th geological parameter of an i-th sample of the experimental shale samples; $x_{ij}$ represents a parameter value of the j-th geological parameter of the i-th sample of the experimental shale samples; $\bar{x}_j$ represents a sample mean of the j-th geological parameter of the experimental shale samples; $S_j$ represents a sample standard deviation of the j-th geological parameter of the experimental shale samples; n represents a number of the experimental shale samples; and m represents a number of the geological parameters of the experimental shale samples;

S22: establishing a correlation coefficient matrix between the geological parameters of the experimental shale samples based on the standardized parameter values of the geological parameters of the experimental shale samples, wherein the correlation coefficient matrix is expressed by formulas (4)-(8) as follows:

$$R = (r_{AB})_{m \times m} \quad (4)$$

$$r_{AB} = \frac{Cov(A, B)}{\sigma_A \times \sigma_B} \quad (5)$$

$$Cov(A, B) = \frac{\sum_{i=1}^{n} (A_i - \bar{A})(B_i - \bar{B})}{n-1} \quad (6)$$

$$\sigma_A = \sqrt{\frac{\sum_{i=1}^{n} (A_i - \bar{A})^2}{n-1}} \quad (7)$$

$$\sigma_B = \sqrt{\frac{\sum_{i=1}^{n} (B_i - \bar{B})^2}{n-1}} \quad (8)$$

where R represents the correlation coefficient matrix; $r_{AB}$ represents a correlation coefficient between a geological parameter A and a geological parameter B; Cov(A, B) represents a covariance between the geological parameter A and the geological parameter B; $\sigma_A$ represents a standard deviation of the geological parameter A, $\sigma_B$ represents a standard deviation of the geological parameter B, $A_i$ and $B_i$ represent values of the i-th sample of the geological parameter A and the geological parameter B, respectively; $\bar{A}$ represents a sample mean of the geological parameter A of the experimental shale samples; and $\bar{B}$ represents a sample mean of the geological parameter B of the experimental shale samples;

S23: calculating eigenvalues, contribution rates, and cumulative contribution rates of the correlation coefficient matrix;
where when the eigenvalues of the correlation coefficient matrix are calculated, a characteristic equation (9) of the correlation coefficient matrix is as follows:

$$|R - \lambda E| = 0 \quad (9)$$

where $\lambda$ represents one of the eigenvalues of the correlation coefficient matrix, and E represents an identity matrix; and
where each of the contribution rates is calculated using a formula (10) as follows:

$$D = \frac{\lambda_k}{\sum_{k=1}^{m} \lambda_k} \quad (10)$$

where D represents the contribution rate, and $\lambda_k$ represents a k-th eigenvalue of the eigenvalues of the correlation coefficient matrix;

S24: determining a number of the principal components representing the variation of the parameters values of the geological parameters of the experimental shale samples and eigenvalues of the principal components based on the cumulative contribution rates;

S25: calculating eigenvectors of the correlation coefficient matrix based on the eigenvalues of the principal components determined in step S24; and S26: obtaining a mathematical expression (11) of the principal components based on the eigenvectors, wherein the mathematical expression (11) is expressed as follows:

$$F_{ik} = \sum_{j=0}^{m} Zx_{ij} \frac{u_{kj}}{\sqrt{\lambda_k}} \quad (11)$$

where $F_{ik}$ represents a k-th principal component of the i-th sample of the experimental shale samples; and $u_{kj}$ represents a j-th element in a k-th eigenvector of the eigenvectors;

S3: performing regression analysis using the principal components as independent variables and the fractal dimensions of the experimental shale samples as dependent variables to obtain a quantitative calculation model for fractal dimensions based on geological parameters; and S4: calculating fractal dimensions of the target shale samples according to the parameter values of the geological parameters of the target shale samples and the quantitative calculation model for fractal dimension based on geological parameters, wherein in the S4, no NMR experiment is required.

6. The calculation method for fractal dimension of shale pores as claimed in claim 5, further comprising:

evaluating, based on the fractal dimensions of the target shale samples, a strength of heterogeneity in pore structure of the target stratum of the study area; determining whether the strength of heterogeneity is smaller than a target strength of heterogeneity; and in response to the strength of heterogeneity being smaller than the target strength of heterogeneity, exploring shale oil and gas on the target stratum of the study area.

* * * * *